US012694514B2

(12) United States Patent
Dekel et al.

(10) Patent No.: US 12,694,514 B2
(45) Date of Patent: Jul. 28, 2026

---

(54) SYSTEMS AND METHODS FOR IDENTIFYING IMAGES CONTAINING INDICATORS OF A CELIAC-LIKE DISEASE

(71) Applicant: Given Imaging LTD., Yoqneam (IL)

(72) Inventors: Eyal Dekel, Haifa (IL); Almog Elharar, Tel Aviv (IL); Stas Rozenfeld, Hod HaSharon (IL)

(73) Assignee: GIVEN IMAGING LTD, Yoqneam (IL)

( * ) Notice: Subject to any disclaimer, the term of this patent is extended or adjusted under 35 U.S.C. 154(b) by 425 days.

(21) Appl. No.: 18/035,417

(22) PCT Filed: Nov. 14, 2021

(86) PCT No.: PCT/IL2021/051353
§ 371 (c)(1),
(2) Date: May 4, 2023

(87) PCT Pub. No.: WO2022/107124
PCT Pub. Date: May 27, 2022

(65) Prior Publication Data
US 2023/0401700 A1     Dec. 14, 2023

Related U.S. Application Data

(60) Provisional application No. 63/115,283, filed on Nov. 18, 2020.

(51) Int. Cl.
*G06T 7/00* (2017.01)
*G16H 50/20* (2018.01)

(52) U.S. Cl.
CPC ........... *G06T 7/0012* (2013.01); *G16H 50/20* (2018.01); *G06T 2207/10068* (2013.01); *G06T 2207/30028* (2013.01)

(58) Field of Classification Search
CPC ......... G06T 7/0012; G06T 2207/10068; G06T 2207/30028; G06T 2207/10016;
(Continued)

(56) References Cited

U.S. PATENT DOCUMENTS 8,768,024 B1 *   7/2014   Zingman .......... A61B 1/000094
                                                              348/45
2010/0046816 A1 *   2/2010   Igual-Munoz ..... G06V 10/7635
                                                              382/128
(Continued)

FOREIGN PATENT DOCUMENTS

WO          2020079667 A1      4/2020

OTHER PUBLICATIONS

International Search Report for application No. PCT/IL2021/051353 dated Feb. 28, 2022 (4 pages).
(Continued)

*Primary Examiner* — Matthew C Bella
*Assistant Examiner* — Andrew B. Jones
(74) *Attorney, Agent, or Firm* — Carter, DeLuca & Farrell, LLP

(57) ABSTRACT

A method for detecting indicators of a disease characterized by a presence of villous atrophy in images of a gastrointestinal tract (GIT), includes accessing a consecutive set of images of a portion of the GIT comprising a small bowel. Each image is associated with one or more classification scores, and each classification score is indicative of the associated image including a respective indicator of a disease characterized by the presence of villous atrophy. The method further includes selecting a subset of images from the consecutive set of images based on the one or more classification scores of each image of the consecutive set of images, identifying a segment of images which includes all of the images that show a proximal portion of the small
(Continued)

bowel, selecting a plurality of images from the identified segment of images that represent the proximal portion of the small bowel, and displaying the selected images.

18 Claims, 12 Drawing Sheets

(58) Field of Classification Search
CPC .......... G06T 2207/20076; G06T 2207/20084; G16H 50/20
See application file for complete search history.

(56) References Cited

U.S. PATENT DOCUMENTS

2019/0244351 A1 * 8/2019 Dolnik ................... G16H 30/40
2024/0394881 A1 * 11/2024 Bangia ................. G06V 10/764

OTHER PUBLICATIONS

Written Opinion of International Search Authority for application No. PCT/IL2021/051353 dated Feb. 28, 2022 (8 pages).
Japanese Office Action for Application No. 2023-529959 dated Aug. 19, 2025 with English translation, 10 pages.

* cited by examiner

Normal Villi

802

Villous Atrophy

804

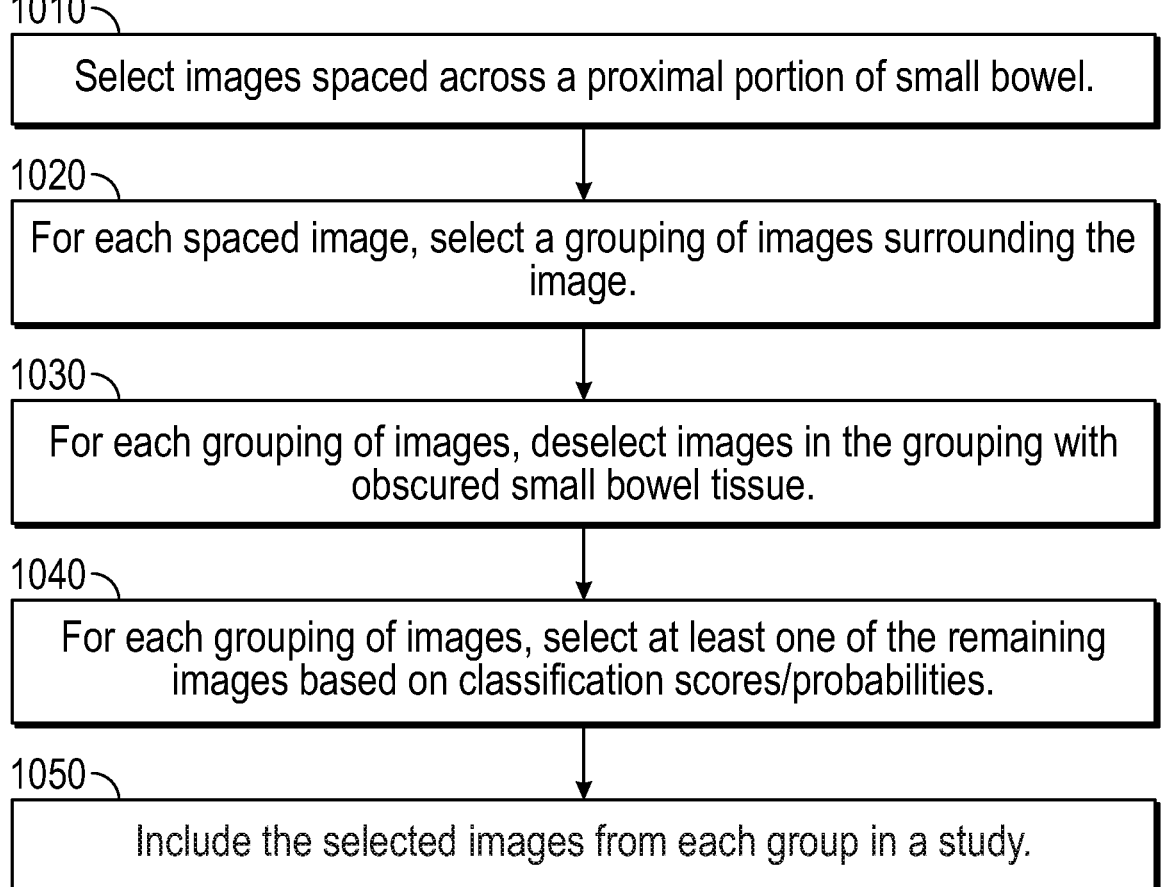

1010

Select images spaced across a proximal portion of small bowel.

1020

For each spaced image, select a grouping of images surrounding the image.

1030

For each grouping of images, deselect images in the grouping with obscured small bowel tissue.

1040

For each grouping of images, select at least one of the remaining images based on classification scores/probabilities.

1050

Include the selected images from each group in a study.

FIG. 10

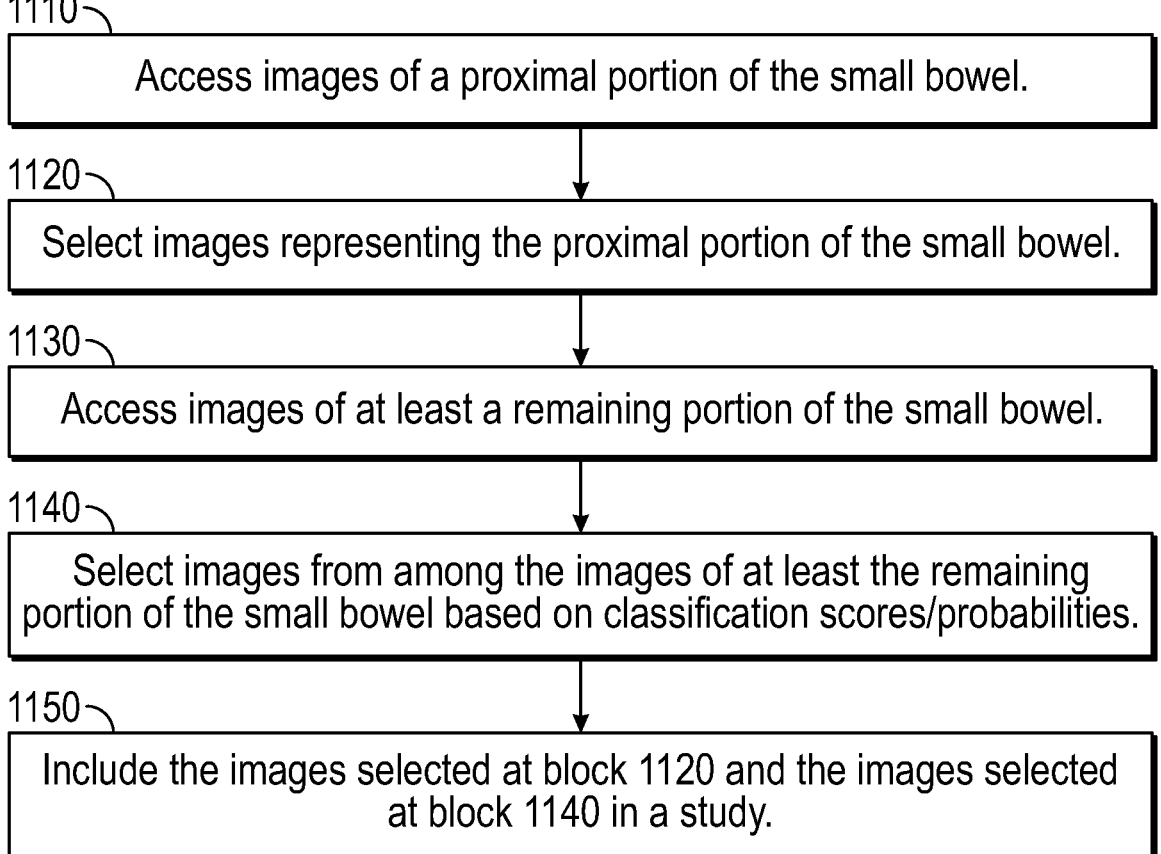

1110
Access images of a proximal portion of the small bowel.

1120
Select images representing the proximal portion of the small bowel.

1130
Access images of at least a remaining portion of the small bowel.

1140
Select images from among the images of at least the remaining portion of the small bowel based on classification scores/probabilities.

1150
Include the images selected at block 1120 and the images selected at block 1140 in a study.

FIG. 11

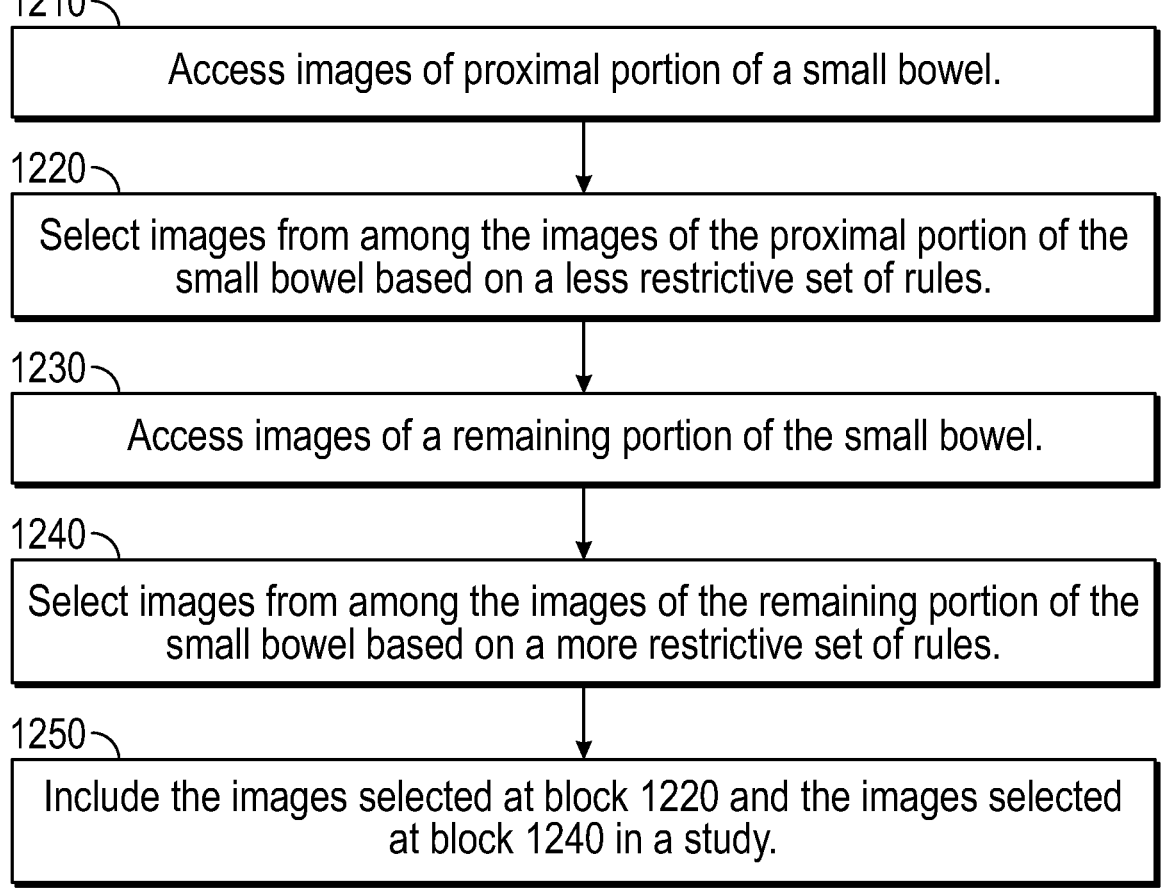

1210
Access images of proximal portion of a small bowel.

1220
Select images from among the images of the proximal portion of the small bowel based on a less restrictive set of rules.

1230
Access images of a remaining portion of the small bowel.

1240
Select images from among the images of the remaining portion of the small bowel based on a more restrictive set of rules.

1250
Include the images selected at block 1220 and the images selected at block 1240 in a study.

FIG. 12

SYSTEMS AND METHODS FOR IDENTIFYING IMAGES CONTAINING INDICATORS OF A CELIAC-LIKE DISEASE

CROSS REFERENCE TO RELATED APPLICATION

This application is a U.S. National Stage Application filed under 35 U.S.C. § 371 (a) of International Patent Application No. PCT/IL2021/051353, filed Nov. 14, 2021, which claims the benefit of and priority to U.S. Provisional Application No. 63/115,283, filed on Nov. 18, 2020. The entire contents of each of the foregoing applications is hereby incorporated by reference herein.

FIELD

The disclosure relates to image analysis methods and systems and, more particularly, to systems and methods for analyzing a stream of images of a gastrointestinal tract to detect indicators of a celiac-like disease.

BACKGROUND

Capsule endoscopy (CE) allows examining the entire gastrointestinal tract (GIT) endoscopically. There are capsule endoscopy systems and methods that are aimed at examining a specific portion of the GIT, such as the small bowel (SB) or the colon. CE is a non-invasive procedure that does not require the patient to be admitted to a hospital, and the patient can continue most daily activities while the capsule is in his body.

On a typical CE procedure, the patient is referred to a procedure by a physician. The patient then arrives at a medical facility (e.g., a clinic or a hospital), to perform the procedure. The capsule, which is about the size of a multivitamin, is swallowed by the patient under the supervision of a health professional (e.g., a nurse or a physician) at the medical facility. According to some CE procedures and methods, the patient is provided with a wearable device, e.g., a sensor belt and a recorder placed in a pouch and strap to be placed around the patient's shoulder. The wearable device may include a storage device. The patient may be given guidance and/or instructions and then released to his daily activities.

The capsule captures images as it travels naturally through the GIT. Images and additional data (e.g., metadata) may be transmitted to the recorder that is worn by the patient. The capsule is typically disposable and passes naturally with a bowel movement. The procedure data (e.g., the captured images or a portion of them and additional metadata) may be stored on the storage device of the wearable device.

The wearable device is typically returned by the patient to the medical facility with the procedure data stored thereon. The procedure data is downloaded to a computing device typically located at the medical facility, which has an engine software stored thereon. Typically, the number of images transferred to be processed is of the order of tens of thousands and about on average. The received procedure data is then processed by the engine to a compiled study (or "study"). Typically, a study includes thousands of images (around 6,000).

A reader (which may be the procedure supervising physician, a dedicated physician, or the referring physician) may access the study via a reader application. The reader then reviews the study, evaluates the procedure, and provides his input via the reader application. Since the reader needs to review thousands of images, the reading time of a study may usually take between half an hour to an hour on average, and the reading task may be tiresome. A report is then generated by the reader application based on the compiled study and the reader's input. On average, it would take an hour to review the study and generate a report. The report may include, for example, images of interest, e.g., images which are identified as including pathologies, selected by the reader; evaluation or diagnosis of the patient's medical condition based on the procedure's data (i.e., the study) and/or recommendations for follow up and/or treatment provided by the reader. The report may then be forwarded to the referring physician. The referring physician may decide on a required follow up or treatment based on the report.

SUMMARY

The present disclosure relates to systems and methods for analyzing a stream of images of a gastrointestinal tract (GIT). In various aspects, the present disclosure relates to systems and methods for analyzing a stream of images to identify celiac-like diseases, e.g., by identifying images that contain indicators of a celiac-like disease, such as images characterized by a presence of villous atrophy in small bowel images of a gastrointestinal tract. The technology of the present disclosure may work with images captured by various capsule endoscopy technologies.

As used herein with respect to a GIT, the term "distal" refers to a direction towards the rectum of the GIT or a portion that is closer to the rectum of the GIT, and the term "proximal" refers to a direction towards the esophagus of the GIT or a portion that is closer to the esophagus of the GIT. Further, to the extent consistent, any or all of the aspects detailed herein may be used in conjunction with any or all of the other aspects detailed herein.

In an aspect of the present disclosure, a method for detecting indicators of a disease characterized by a presence of villous atrophy in images of a gastrointestinal tract (GIT), includes accessing a consecutive set of images of at least a portion of the GIT comprising a small bowel. Each image is associated with one or more classification scores, and each classification score of the one or more classification scores is indicative of the associated image including a respective indicator of a disease characterized by the presence of villous atrophy. The method further includes selecting a subset of images from the consecutive set of images based on the one or more classification scores of each image of the consecutive set of images, identifying from the consecutive set of images a segment of images which includes all of the images that show a proximal portion of the small bowel, selecting a plurality of images from the identified segment of images that represent the proximal portion of the small bowel, and displaying the selected plurality of identified images and the subset of images on a display.

In another aspect of the present disclosure, the proximal portion of the small bowel may include a duodenum.

In another aspect of the present disclosure, the disease characterized by the presence of villous atrophy may include human immunodeficiency virus, common variable immune deficiency, Chron's disease, and/or celiac disease.

In still another aspect of the present disclosure, selecting the plurality of images from the identified segment of images may be based on the one or more classification scores.

In yet another aspect of the present disclosure, selecting the plurality of images from the segment of images that represents the proximal portion of the small bowel includes selecting images spaced across the proximal portion of the small bowel.

In an aspect of the present disclosure, selecting images spaced across the proximal portion of the small bowel includes selecting images of the proximal portion of the small bowel which are not obscured.

In an aspect of the present disclosure, the method may further include detecting one or more indicators of a disease associated with the presence of villous atrophy in the consecutive set of images based on at least one of a deep learning classifier or a classical machine learning classifier.

In another aspect of the present disclosure, the method may further include selecting the plurality of images from the identified segment of images includes uniformly sampling the proximal portion of the small bowel based on time or length of the small bowel, where length is based on at least one of a number of images in the consecutive set of images or an estimated advance of a capsule endoscopy device along the small bowel.

In an aspect of the present disclosure, selecting the plurality of images from the identified segment of images may include dividing the plurality of images from the identified segment of images into a predetermined number of sampling points, and for each sampling point, selecting one or more images from a predetermined range of images surrounding the sampling point.

In another aspect of the present disclosure, the indicator may include scalloping of the mucosa of the small bowel, mosaic patterning of the mucosa of the small bowel, and/or atrophy of villi of the small bowel.

Provided in accordance with aspects of the disclosure is a method for detecting indicators of a disease characterized by a presence of villous atrophy in images of a gastrointestinal tract (GIT). The method includes accessing a consecutive set of images of at least a portion of the GIT comprising a small bowel. Each image is associated with one or more classification scores, and each classification score of the one or more classification scores is indicative of the associated image including a respective indicator of a disease characterized by the presence of villous atrophy. The method further includes dividing the consecutive set of images into image sets. The image sets include images of a pre-small bowel, images of a proximal portion of the small bowel, and images of a remaining portion of the small bowel. The method further includes selecting a first subset of images from the images of the proximal portion of the small bowel based on application of a first set of rules, where at least one rule of the first set of rules is based on the one or more classification scores associated with each image, selecting a second subset of images from the images of the remaining portion of the small bowel based on application of a second set of rules different from the first set of rules, where at least one rule of the second set of rules is based on the one or more classification scores associated with each image, and displaying the selected first and second subsets of images on a display.

In still another aspect of the present disclosure, the second set of rules may be more selective than the first set of rules.

In another aspect, the first set of rules is configured to provide a more comprehensive representation of the proximal portion of the small bowel and the second set of rules is configured to provide a less comprehensive representation of the remaining portion of the small bowel or of at least the remaining portion of the small bowel. For example, the first set of rules may include one or more rules for selecting images which represent the entire proximal portion of the SB, while the second set of rules may include one or more rules for selecting only images which represent areas of the SB identified to display indicators of a celiac-like disease. An exemplary result of such first and second rule sets for the different portions of the SB is that fewer images would be selected per unit length of small bowel from the second subset of images than the images selected by the first subset of images.

In an aspect of the present disclosure, the indicator may include scalloping of the mucosa of the small bowel, mosaic patterning of the mucosa of the small bowel, and/or atrophy of villi of the small bowel.

In another aspect of the present disclosure, the disease characterized by the presence of villous atrophy may include human immunodeficiency virus, common variable immune deficiency, Chron's disease, and/or celiac disease.

In another aspect of the present disclosure, the proximal portion of the small bowel may include a duodenum.

In still another aspect of the present disclosure, the method includes providing the one or more classification scores by a deep learning classifier and/or a classical machine learning classifier.

Provided in accordance with aspects of the disclosure is a system for detecting indicators of a celiac-like disease. The system includes one or more processors and at least one memory. The memory includes instructions stored thereon which, when executed by the one or more processors, cause the system to: access images of a proximal portion of the small bowel, select images from among the images of the proximal portion of the small bowel based on a first set of rules, access images of at least a remaining portion of the small bowel, and select images from among the images of at least the remaining portion of the small bowel based on a second set of rules different from the first set of rules.

In an aspect of the present disclosure, selecting images from among the images of the proximal portion of the small bowel based on the first set of rules includes selecting images representing the proximal portion of the small bowel, and selecting images from among the images of at least the remaining portion of the small bowel based on the second set of rules includes selecting images from among the images of at least the remaining portion of the small bowel based on one or more classification scores indicative of an image including a respective indicator of a celiac-like disease.

In an aspect of the present disclosure, selecting images from among the images of the proximal portion of the small bowel based on a first set of rules includes selecting images from among the images of the proximal portion of the small bowel based on one or more classification scores indicative of an image including a respective indicator of a celiac-like disease, and selecting images from among the images of at least the remaining portion of the small bowel based on the second set of rules includes selecting images from among the images of the remaining portion of the small bowel based on one or more classification scores indicative of an image including a respective indicator of a celiac-like disease.

In an aspect of the present disclosure, the second set of rules is more selective than the first set of rules.

BRIEF DESCRIPTION OF DRAWINGS

The above and other aspects and features of the disclosure will become more apparent in view of the following detailed description when taken in conjunction with the accompanying drawings wherein like reference numerals identify similar or identical elements.

FIG. 10 is a flow diagram of an exemplary operation for identifying images of a proximal portion of a small bowel, in accordance with aspects of the disclosure;

FIG. 11 is a flow diagram or an exemplary operation for selecting images, in accordance with aspects of the disclosure; and FIG. 12 is a flow diagram of another exemplary operation for selecting images, in accordance with aspects of the disclosure.

DETAILED DESCRIPTION

Figure 1:
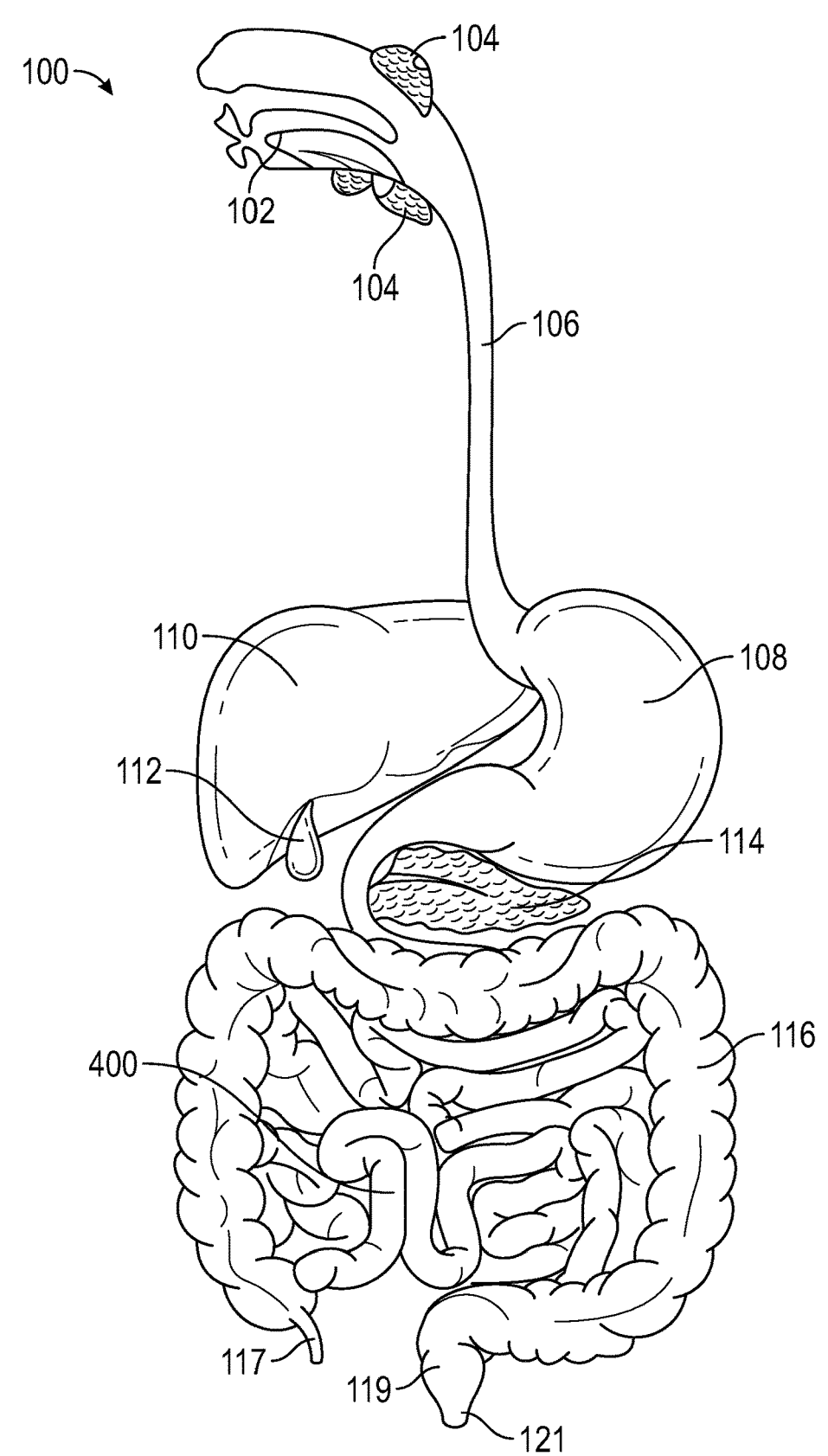
FIG. 1 is a diagram illustrating a gastrointestinal tract (GIT)

The disclosure relates to systems and methods for analyzing medical images. In various aspects, the disclosure relates to systems and methods for identifying images which include indicators of a celiac-like disease, such as images characterized by a presence of villous atrophy in the small bowel mucosa in a stream of images captured in vivo via a Capsule Endoscopy (CE) procedure. The technology of the present disclosure may work with capsule endoscopy images captured by various technologies. Generally, the present disclosure provides systems and methods which operate to aid a clinician in correctly and accurately diagnosing a celiac-like disease in a patient, without spending an inordinate amount of time reviewing a large number of images. Accordingly, the technology of the present disclosure can enable a clinician to make a correct and accurate diagnosis of a celiac-like disease by reviewing a reasonably or relatively compact number of images and without missing important information.

In the following detailed description, specific details are set forth in order to provide a thorough understanding of the disclosure. However, it will be understood by those skilled in the art that the disclosure may be practiced without these specific details. In other instances, well-known methods, procedures, and components have not been described in detail so as not to obscure the present disclosure. Some features or elements described with respect to one system may be combined with features or elements described with respect to other systems. For the sake of clarity, discussion of the same or similar features or elements may not be repeated.

Although the disclosure is not limited in this regard, discussions utilizing terms such as, for example, "processing," "computing," "determining," "analyzing," "checking," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes.

Although the disclosure is not limited in this regard, the terms "plurality" and "a plurality" as used herein may include, for example, "multiple" or "two or more." The terms "plurality" or "a plurality" may be used throughout the specification to describe two or more components, devices, elements, units, parameters, or the like. The term "set," when used herein, may include one or more items. Unless explicitly stated, the methods described herein are not constrained to a particular order or sequence. Additionally, some of the described methods or elements thereof can occur or be performed simultaneously, at the same point in time, or concurrently.

The terms "image" and "frame" may each refer to or include the other and may be used interchangeably in the present disclosure to refer to a single capture by an imaging device. For convenience, the term "image" may be used more frequently in the present disclosure, but it will be understood that references to an image shall apply to a frame as well.

The term "classification score(s)" or "score(s)" may be used throughout the specification to indicate a value or a vector of values for a category or a set of categories applicable to an image/frame. In various implementations, the value or vector of values of a classification score or classification scores may be or may reflect probabilities. The term "classification probabilities" may be used throughout the specification to describe a result of transforming classification scores into values which reflect probabilities that each category of the set of categories applies to the image/frame. The model providing a classification score or classification probability may be a machine learning system or may be a non-machine learning system. In various embodiments, a model may output classification scores, which may be probabilities or may be transformed into classification probabilities. In various embodiments, a model may output classification probabilities. Aspects of the present disclosure may be described using the term "classification score" or the term "classification probability." It is intended that descriptions using "classification score" shall be applicable to "classification probability" as well, and vice versa.

As used herein, "deep learning neural network" refers to and includes a neural network having several hidden layers and which does not require feature selection or feature engineering. A "classical" machine learning system, in contrast, is a machine learning system which requires feature selection or feature engineering.

The term "celiac-like disease" refers to and includes celiac disease as well as other diseases which present pathologies and/or morphological characteristics of the villi, such as villous atrophy, similar to celiac disease, such as, without limitation, human immunodeficiency virus, common variable immune deficiency, and Chron's disease, among others.

The term "location" and its derivatives, as referred to herein with respect to an image, may refer to the estimated location of the capsule along the GIT while capturing the image or to the estimated location of the portion of the GIT shown in the image along the GIT.

A type of CE procedure may be determined based on, inter alia, the portion of the GIT that is of interest and is to be imaged (e.g., the colon or the small bowel ("SB")), or based on the specific use (e.g., for checking the status of a GI disease, such as Crohn's disease, or for colon cancer screening).

The terms "surrounding" or "adjacent," as referred to herein with respect to images (e.g., images that surround another image(s), or that are adjacent to other image(s)), may relate to spatial and/or temporal characteristics unless specifically indicated otherwise. For example, images that surround or are adjacent to other image(s) may be images that are estimated to capture sites located near other sites captured by the other image(s) along the GIT and/or images that were captured near the capture time of another image, within a certain threshold, e.g., within one or two centimeters, or within one, five, or ten seconds.

The terms "GIT" and "a portion of the GIT" may each refer to or include the other, according to their context. Thus, the term "a portion of the GIT" may also refer to the entire GIT, and the term "GIT" may also refer only to a portion of the GIT.

The term "proximal portion of the small bowel" refers to and includes a portion of the small bowel from the beginning of the small bowel to a point before the halfway point of the small bowel, such that the physical length of the proximal portion of the small bowel is less than half of the physical length of the small bowel.

Referring to FIG. 1, an illustration of the GIT 100 is shown. The GIT 100 is an organ system within humans and other animals. The GIT 100 generally includes a mouth 102 for taking in sustenance, salivary glands 104 for producing saliva, an esophagus 106 through which food passes aided by contractions, a stomach 108 to secret enzymes and stomach acid to aid in digesting food, a liver 110, a gall bladder 112, a pancreas 114, a small intestine 400 (e.g., SB) for the absorption of nutrients, and a colon 116 (e.g., large intestine) for storing water and waste material as feces prior to defecation. The colon 116 generally includes an appendix 117, a rectum 119, and an anus 121. Food taken in through the mouth is digested by the GIT to take in nutrients, and the remaining waste is expelled as feces through the anus 121.

Studies of different portions of the GIT 100, e.g., SB 400, colon 116, esophagus 106, and/or stomach 108 may be presented via a suitable user interface. As used herein, the term "study" refers to and includes at least a set of images selected from the images captured by a CE imaging device (e.g., 212, FIG. 2) during a single CE procedure performed with respect to a specific patient and at a specific time and can optionally include information other than images as well. The type of procedure performed may determine which portion of the GIT 100 is the portion of interest. Examples of types of procedures performed include, without limitation, an SB procedure, a colon procedure, an SB and colon procedure, a procedure aimed to specifically exhibit or check the SB, a procedure aimed to specifically exhibit or check the colon, a procedure aimed to specifically exhibit or check the colon and the SB, or a procedure to exhibit or check the entire GIT: esophagus, stomach, SB, and colon.

Figure 2:
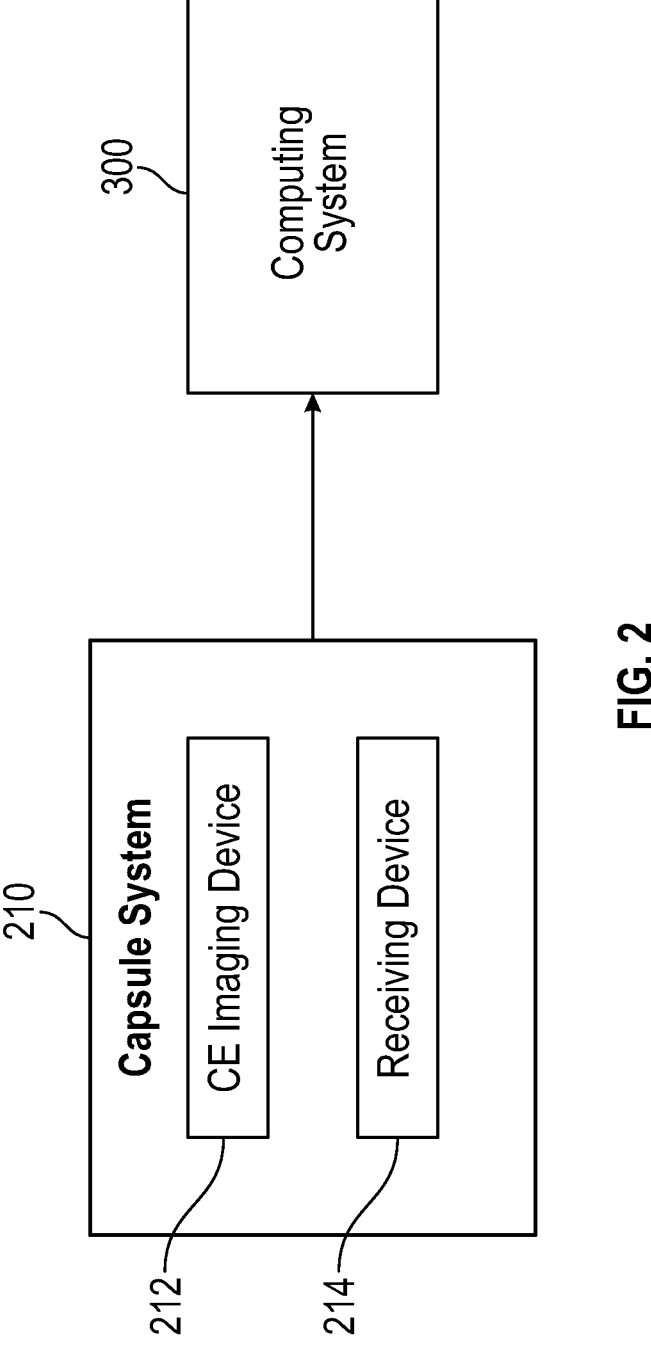
FIG. 2 is a block diagram of an exemplary system for analyzing medical images captured in vivo via a Capsule Endoscopy (CE) procedure in accordance with aspects of the disclosure.

FIG. 2 shows a block diagram of an exemplary system for analyzing medical images captured in vivo via a CE procedure. The system generally includes a capsule system 210 configured to capture images of the GIT, and a computing system 300 (e.g., local system and/or cloud system) configured to process the captured images.

The capsule system 210 may include a swallowable CE imaging device 212 (e.g., a capsule) configured to capture images of the GIT as the CE imaging device 212 travels through the GIT. The images may be stored on the CE imaging device 212 and/or transmitted to a receiving device 214, typically including an antenna. In some capsule systems 210, the receiving device 214 may be located on the patient who swallowed the CE imaging device 212 and may, for example, take the form of a belt worn by the patient or a patch secured to the patient.

The capsule system 210 may be communicatively coupled with the computing system 300 and can communicate captured images to the computing system 300. The computing system 300 may process the received images using image processing technologies, machine learning technologies, and/or signal processing technologies, among other technologies. The computing system 300 can include local computing devices that are local to the patient and/or the patient's treatment facility, a cloud computing platform that is provided by cloud services, or a combination of local computing devices and a cloud computing platform.

In the case where the computing system 300 includes a cloud computing platform, the images captured by the capsule system 210 may be transmitted online, during the procedure, to the cloud computing platform. In various embodiments, the images can be transmitted via the receiving device 214 worn or carried by the patient. In various embodiments, the images can be transmitted via the patient's smartphone or via any other device connected to the Internet and which may be coupled with the CE imaging device 212 or the receiving device 214.

Figure 3:
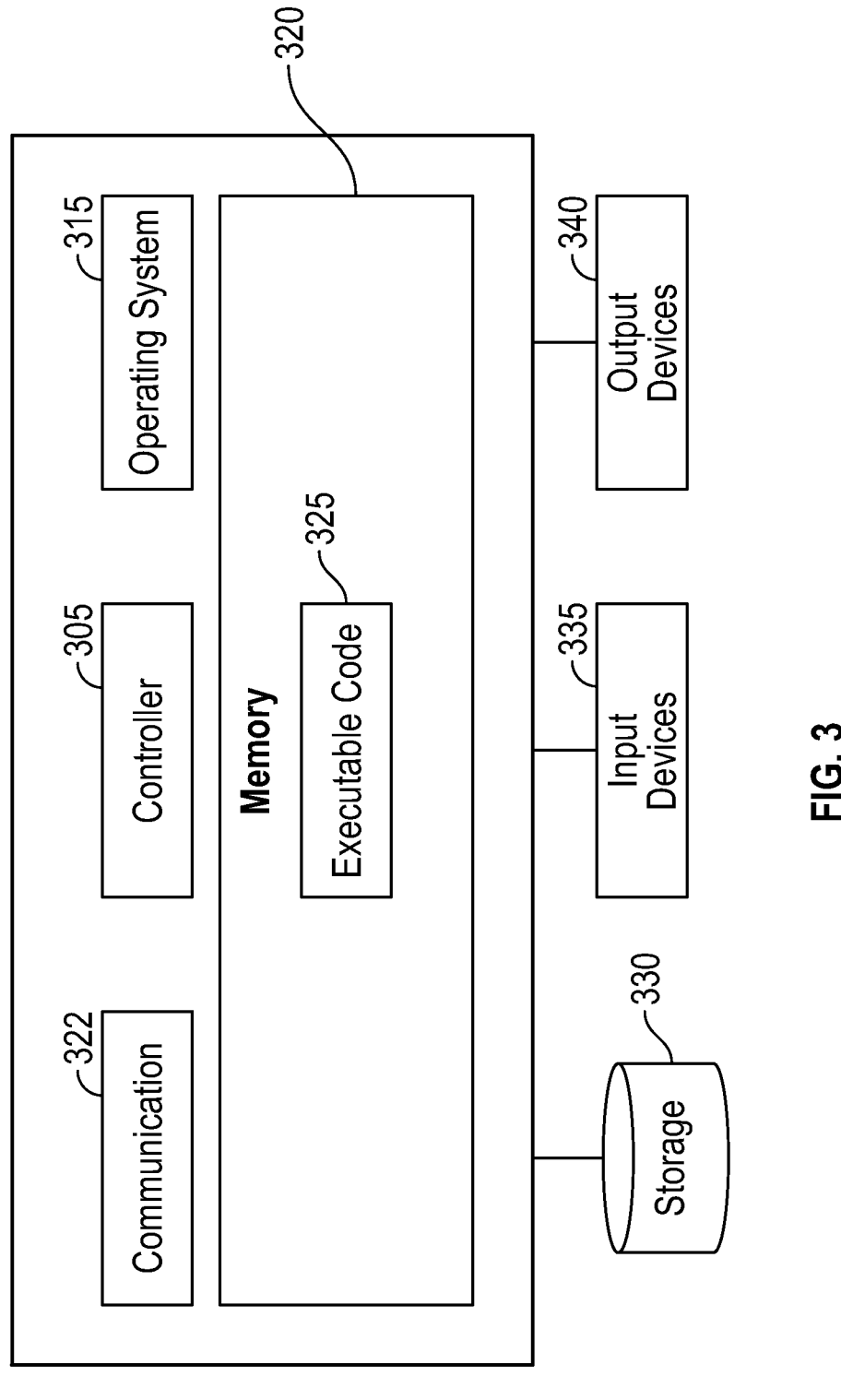
FIG. 3 is a block diagram of an exemplary computing device which may be used with aspects of the disclosure.

FIG. 3 shows a high-level block diagram of an exemplary computing system 300 that may be used with image analyzing systems of the present disclosure. Computing system 300 may include a processor or controller 305 that may be or include, for example, one or more central processing unit processor(s) (CPU), one or more Graphics Processing Unit(s) (GPU or GPGPU), a chip or any suitable computing or computational device, an operating system 215, a memory 320, a storage 330, input devices 335 and output devices 340. Modules or equipment for collecting or receiving (e.g., a receiver worn on a patient) or displaying or selecting for display (e.g., a workstation) medical images collected by the CE imaging device 212 (FIG. 2) may be or include, or may be executed by, the computing system 300 shown in FIG. 3. A communication component 322 of the computing system 300 may allow communications with remote or external devices, e.g., via the Internet or another network, via radio, or via a suitable network protocol such as File Transfer Protocol (FTP), etc.

The computing system 300 includes an operating system 315 that may be or may include any code segment designed and/or configured to perform tasks involving coordination, scheduling, arbitration, supervising, controlling or otherwise managing operation of computing system 300, for example, scheduling execution of programs. Memory 320 may be or may include, for example, a Random Access Memory (RAM), a read-only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 320 may be or may include a plurality of possibly different memory units. Memory 320 may store, for example, instructions to carry out a method (e.g., executable code 325), and/or data such as user responses, interruptions, etc.

Executable code 325 may be any executable code, e.g., an application, a program, a process, task, or script. Executable code 325 may be executed by controller 305, possibly under the control of operating system 315. For example, execution of executable code 325 may cause the display or selection for display of medical images as described herein. In some systems, more than one computing system 300 or components of computing system 300 may be used for multiple functions described herein. For the various modules and functions described herein, one or more computing systems 300 or components of computing system 300 may be used. Devices that include components similar or different to those included in the computing system 300 may be used and may be connected to a network and used as a system. One or more processor(s) 305 may be configured to carry out methods of the present disclosure by, for example, executing software or code. Storage 330 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, medical images, image streams, etc. may be stored in storage 330 and may be loaded from storage 330 into memory 320 where it may be processed by controller 305. In some embodiments, some of the components shown in FIG. 3 may be omitted.

Input devices 335 may include, for example, a mouse, a keyboard, a touch screen or pad, or any suitable input device. It will be recognized that any suitable number of input devices may be operatively coupled to computing system 300. Output devices 340 may include one or more monitors, screens, displays, speakers and/or any other suitable output devices. It will be recognized that any suitable number of output devices may be operatively coupled to computing system 300 as shown by block 340. Any applicable input/output (I/O) devices may be operatively coupled to computing system 300, for example, a wired or wireless network interface card (NIC), a modem, printer or facsimile machine, a universal serial bus (USB) device or external hard drive may be included in input devices 335 and/or output devices 340.

Multiple computer systems 300, including some or all of the components shown in FIG. 3 may be used with the described systems and methods. For example, a CE imaging device 212, a receiver, a cloud-based system, and/or a workstation or portable computing device for displaying images may include some or all of the components of the computer system of FIG. 3. A cloud platform (e.g., a remote server) including components such as computing system 300 of FIG. 3 may receive procedure data such as images and metadata, processes and generate a study, and may also display the generated study for the doctor's review (e.g., on a web browser executed on a workstation or portable computer). An "on-premises" option may use a workstation or local server of a medical facility to store, process and display images and/or a study.

According to some aspects of the present disclosure, a user (e.g., a physician), may build his or her understanding of a case by reviewing a study, which includes a display of images (e.g., captured by the CE imaging device 212) that were selected, e.g., automatically, as images that may be of interest.

Figure 4:
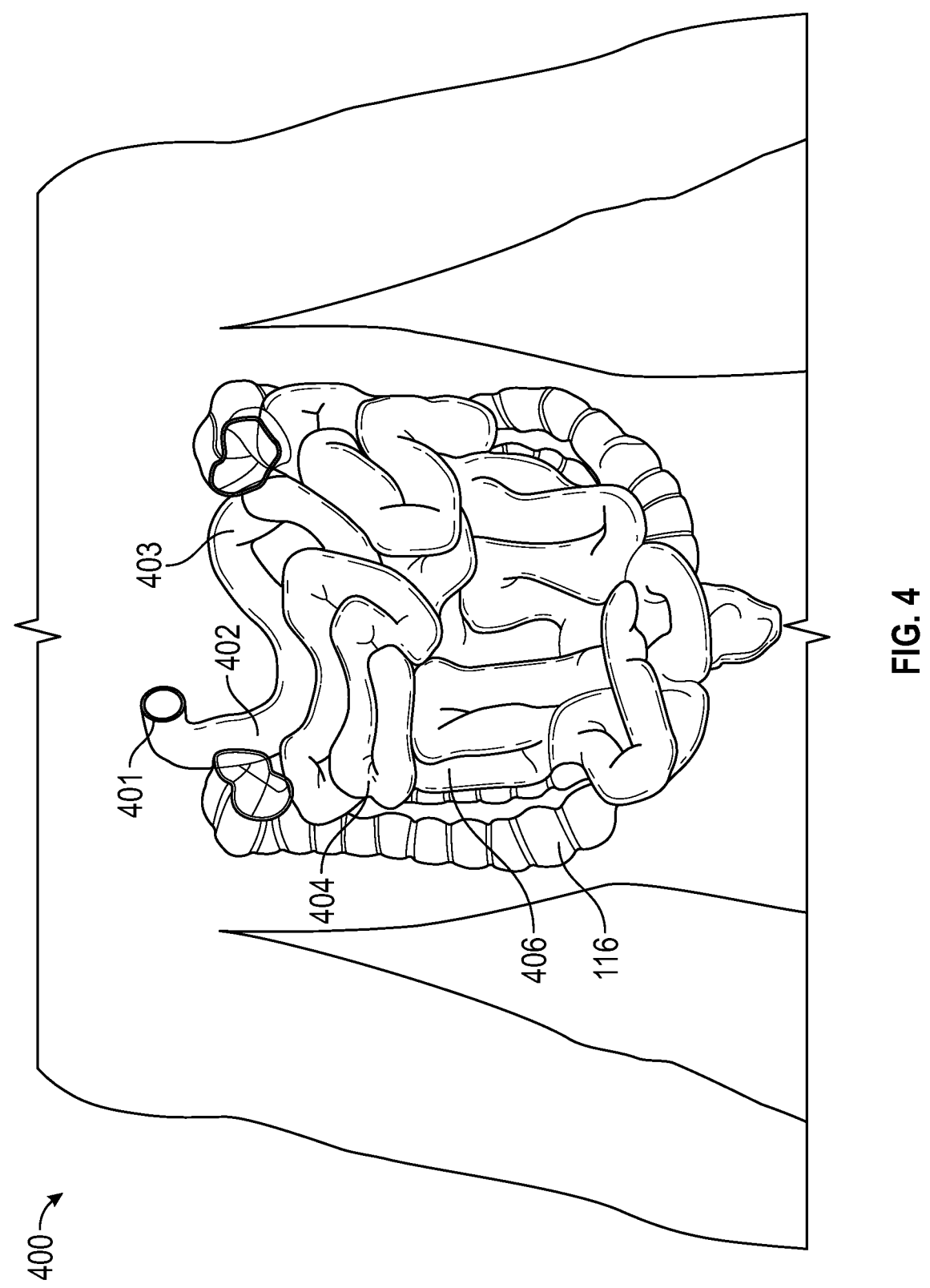
FIG. 4 is a diagram illustrating a small intestine.

With reference to FIG. 4, an illustration of the SB 400 (e.g., small bowel/small intestine) is shown. The SB 400 absorbs nutrients and receives bile and pancreatic juice to aid in digestion. The SB 400 may be divided, for example, into three anatomical segments: the duodenum 402, the jejunum 404, and the ileum 406.

The duodenum 402 (e.g., proximal intestine) is the first section of the SB 400. The duodenum 402 is typically about 5% of the total SB 400 length (i.e., physical length). The duodenum 402 connects the stomach 108 (FIG. 1) to the jejunum 404 and receives bile from the liver/gallbladder and receives pancreatic juice containing digestive enzymes from the pancreas. Food in the duodenum mixes with the bile and the digestive juices. The duodenum 402 begins with the duodenal bulb 401 and ends at the suspensory muscles 403 of the duodenum.

The interior surface of the small bowel 400 is covered in small finger-like protrusions of mucosa called villi 1002 (FIG. 10). The villi 1002 (FIG. 10) contains large numbers of capillaries that, for example, take the amino acids and glucose produced by digestion to the hepatic portal vein and the liver (not shown). Villi are located throughout the small bowel 400, and they operate to increase the internal surface area of the small bowel walls to increase surface area for absorption of digested nutrients.

The jejunum 404 is the second part of the SB 400. The lining of the jejunum 404 is specialized for the absorption by enterocytes of small nutrient molecules that have been previously digested by enzymes in the duodenum 402. The division between the jejunum 404 and ileum 406 is not anatomically distinct.

The ileum 406 (e.g., distal intestine) is the final section of the SB 400, and the distal anatomy of the ileum 406 may be referred to as the terminal ileum. The ileum 406 absorbs vitamin B12, bile salts, and whatever products of digestion were not absorbed by the jejunum 404. The ileum 406 follows the duodenum 402 and jejunum 404, and the terminal ileum is separated from the cecum (not shown) by the ileocecal valve (not shown).

In general, the detection of celiac-like diseases may be performed, for example, based on images captured by a CE imaging device (e.g., 212, FIG. 2). Processing of such images may be performed, for example, based on machine learning techniques, including neural networks, deep-learning neural networks, and/or classical machine learning systems. An example of a neural network is described in connection with FIG. 5 and FIG. 6, and an example of a classical machine learning system is described below. For now, it is sufficient to note that the processing may operate to identify images containing indicators of a celiac-like disease, such as specific pathologies (e.g., villous atrophy) and/or morphological characteristics of the small bowel mucosa (e.g., mosaic pattern, scalloping), among other indicators.

Figure 7C:
FIG. 7C is an exemplary diagram of villous atrophy in accordance with aspects of the disclosure.

Celiac disease is a disorder that affects the SB 400. Celiac disease may be caused by a reaction to gluten, which is a group of proteins often found in wheat. Diagnosis is typically made by a combination of blood antibody tests and intestinal biopsies. Celiac disease may be characterized by various pathologies and morphologies on portions of the SB 400, including, for example, scalloping of the mucosa (FIG. 7A), mosaic patterning of the mucosa (FIG. 7B), and/or villous atrophy (FIGS. 7C and 10B). Villous atrophy occurs when the villi erode away and leave a substantially smaller surface area for absorption of nutrients than the surface area provided by normal villi. Scalloping and mosaic patterning of the mucosa are visual characteristics that may appear once villous atrophy becomes significant. Persons skilled in the art will understand villous atrophy and scalloping and mosaic patterning of the mucosa.

Figure 5:
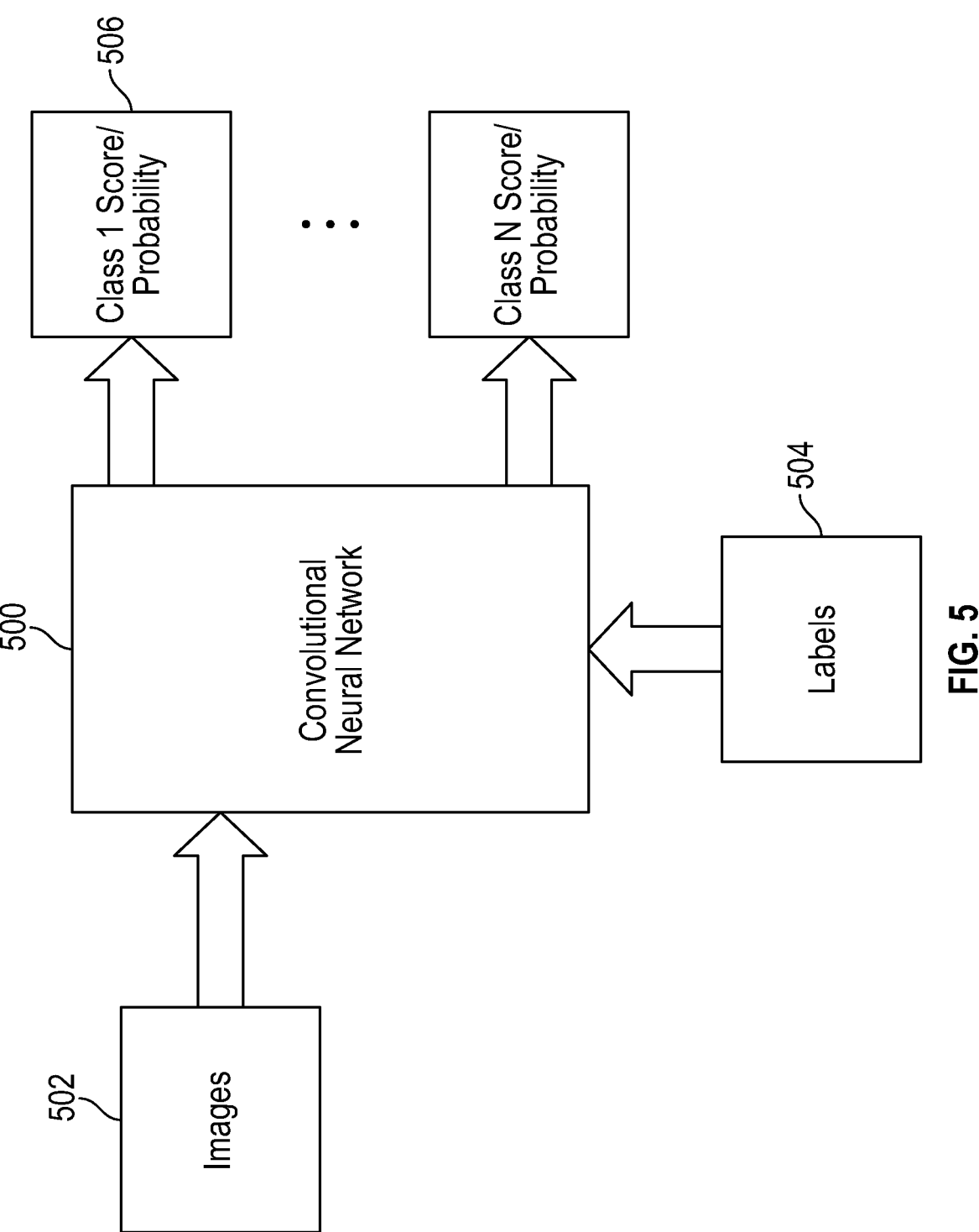
FIG. 5 is a diagram of an exemplary convolutional neural network in accordance with aspects of the disclosure.
Figure 6:
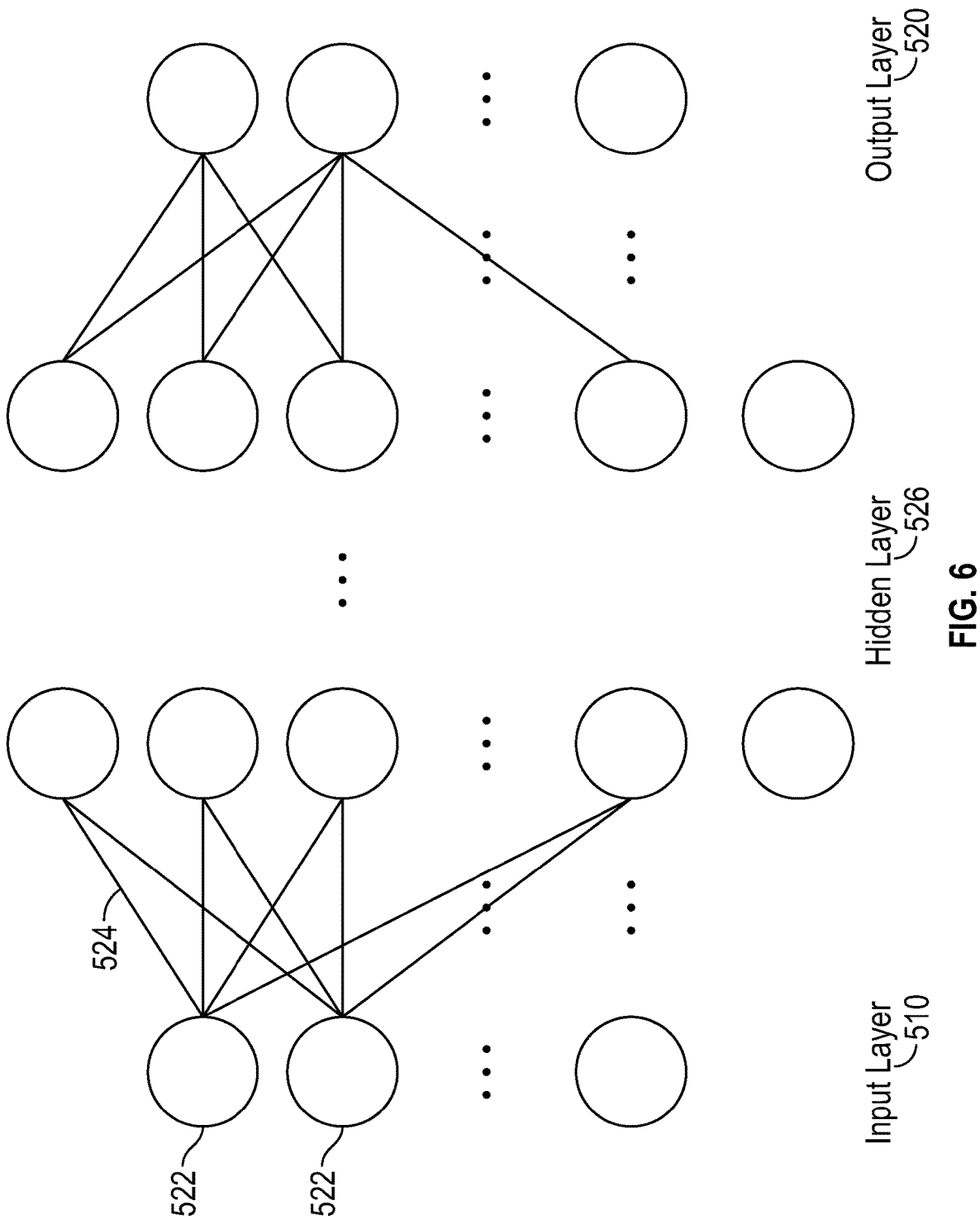
FIG. 6 is a diagram of an exemplary deep learning neural network in accordance with aspects of the disclosure.

With reference to FIG. 5, a block diagram is shown for a convolutional neural network 500 for classifying images in accordance with aspects of the present disclosure. In some systems, the convolutional neural network 500 ("CNN") may be a deep learning neural network (as shown in FIG. 6). As explained in more detail below, the convolutional neural network 500 may operate to output classification scores or probabilities for one or more images taken by a CE imaging device (e.g., 212, FIG. 2). In various methods, more than one CNN may be used, such as a CNN trained using villous atrophy images, a separate CNN trained using scalloping images, and/or a separate CNN trained using mosaic patterning images. In various methods, a CNN may be trained using villous atrophy images, scalloping images, and mosaic patterning images. Other variations are contemplated to be within the scope of the present disclosure. The convolutional neural network 500 may be executed on a computer system, such as the computer system 300 (FIG. 3). Persons skilled in the art will understand the convolutional neural network 500 and how to implement it, and certain details are described below.

In machine learning, a CNN is a class of artificial neural networks (ANN) most commonly applied to analyzing visual imagery. The convolutional aspect of a CNN relates to applying matrix processing operations to localized portions of an image, and the results of those operations (which can involve dozens of different parallel and serial calculations) are sets of many features that are delivered to the next layer. A CNN typically includes convolution layers, activation function layers, and pooling (typically max pooling) layers to reduce dimensionality without losing too many features. Additional information may be included in the operations that generate these features. Providing unique information that yields features that give the neural networks information can be used to ultimately provide an aggregate way to differentiate between different data input to the neural networks.

Referring to FIG. 6, a convolutional neural network implemented as a deep learning neural network may include an input layer 510, a plurality of hidden layers 526, and an output layer 520. The input layer 510, the plurality of hidden layers 526, and the output layer 520 are all comprised of neurons 522 (e.g., nodes). The neurons 522 between the various layers are interconnected via weights 524. Each neuron 522 in the deep learning neural network computes an output value by applying a specific function to the input values coming from the previous layer. The function that is applied to the input values is based on the vector of weights 524 and/or a bias. Learning in the deep learning neural network progresses by making iterative adjustments to these biases and/or weights. The vector of weights 524 and the bias may be referred to as filters (e.g., kernels) and may represent particular features of the input (e.g., a particular shape). The deep learning neural network may output logits. Various types of deep learning neural networks may be used, including MobileNet, Inception, and InceptionResnet, among others.

Referring again to FIG. 5, the convolutional neural network 500 may be trained based on labeled training images and/or objects in training images. For example, an image may be labeled as containing scalloping of the mucosa and/or containing villous atrophy. In such methods and in accordance with this disclosure, the training using labeled images may be referred to as supervised learning. The training further may include augmenting the training images by adding noise, changing colors, hiding portions of the training images, scaling of the training images, rotating the training images, and/or stretching the training images, among other variations. Persons skilled in the art will understand training the convolutional neural network 500 and how to implement it.

In some methods in accordance with this disclosure, the convolutional neural network 500 may provide one or more classification scores or probabilities 506 for images 502 captured by the CE imaging device 212 (see FIG. 2). In the case of classification scores, if the scores are scaled, e.g., using a SoftMax function, the resulting classification probabilities can indicate a probability, such as a probability that the image 502 includes an indicator indicating the presence of a celiac-like disease. For example, the classification scores/probabilities 506 may include a score/probability of the image containing scalloping of the mucosa, a score/probability of the image containing mosaic patterning of the mucosa, and/or a score/probability of the image containing villous atrophy. In various embodiments, the classification scores/probabilities 506 may be outputs (e.g., logits) of a deep learning neural network (e.g., FIG. 6) after applying a function such as a SoftMax to make the outputs represent probabilities.

The aspects and embodiments described in connection with FIG. 5 and FIG. 6 are exemplary and variations are contemplated to be within the scope of the present disclosure. For example, in accordance with aspects of the present disclosure, a classical machine learning system can be used in cooperation with or in place of a deep learning neural network. As described above, the term "classical machine learning system" refers to and includes a machine learning system which requires feature selection and/or feature engineering for inputs to the machine learning system. In contrast, a deep learning neural network is an example of a machine learning system that does not require feature engineering or feature selection. In various embodiments, a classical machine learning system may utilize linear logistic regression and/or a support vector machine, or other classical machine learning techniques which persons skilled in the art will understand.

Figure 7B:
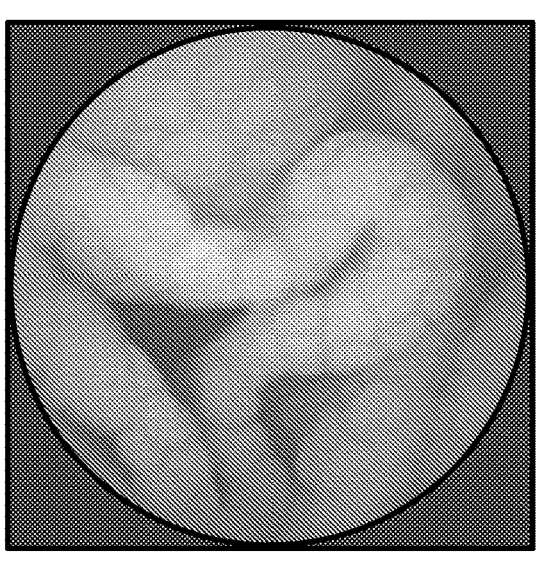
FIG. 7B is an exemplary image of mosaic patterning of the mucosa in accordance with aspects of the disclosure.
Figure 7A:
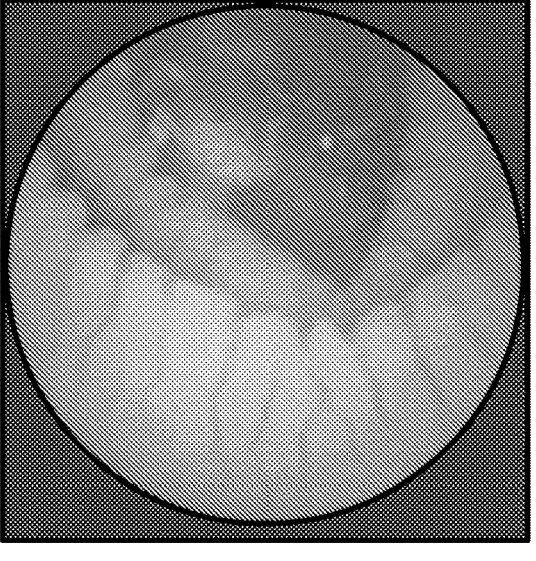
FIG. 7A is an exemplary image of scalloping of the mucosa in accordance with aspects of the disclosure.
Figure 8A:
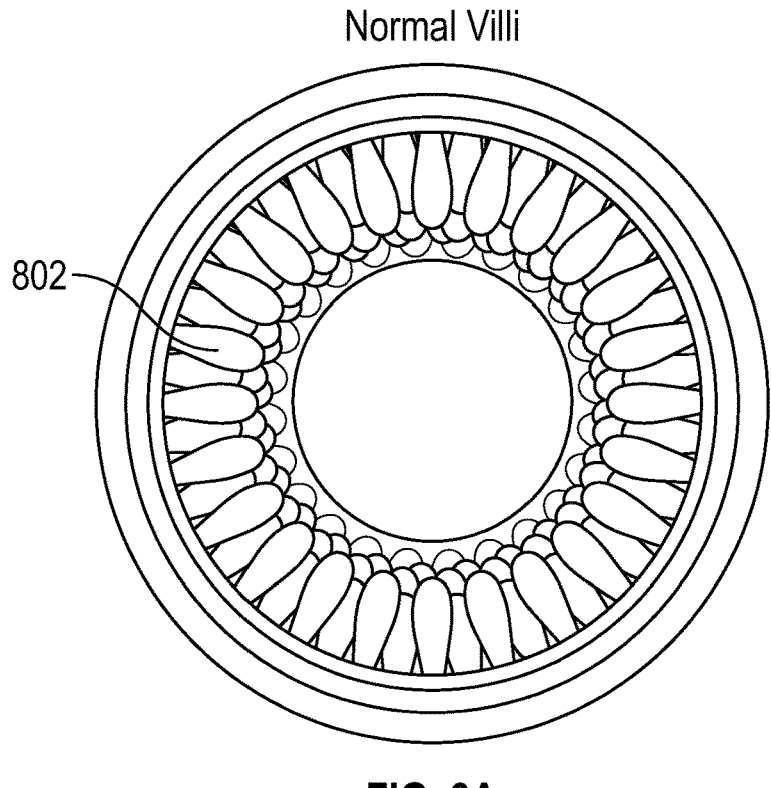
FIG. 8A is a diagram of normal villi in accordance with aspects of the disclosure.
Figure 8B:
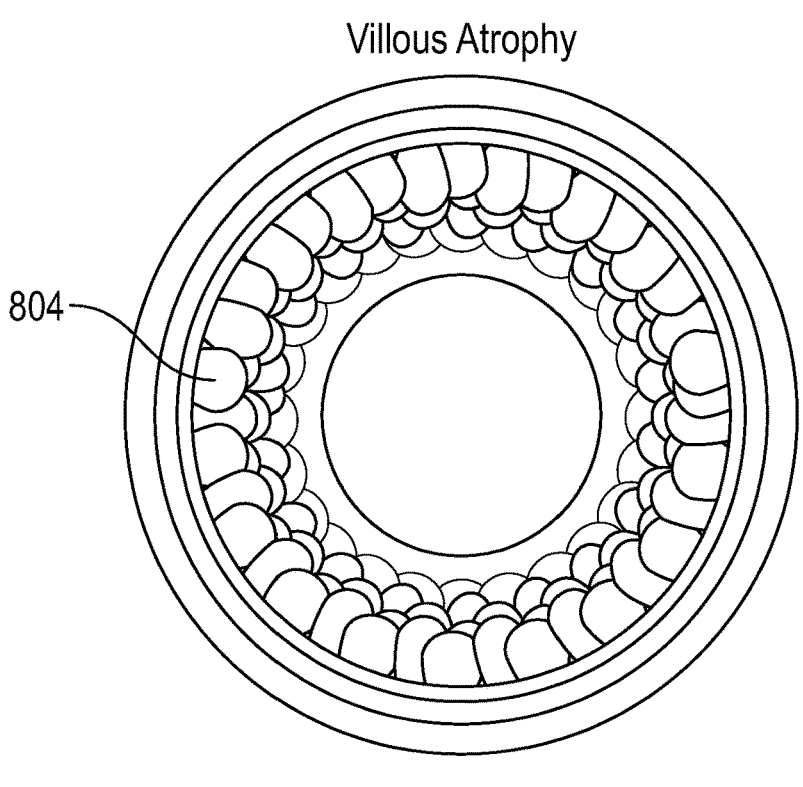
FIG. 8B is a diagram of exemplary villous atrophy in accordance with aspects of the disclosure.

As mentioned above, the input images for training a convolutional neural network (e.g., 500, FIG. 5) may include images of healthy small bowel as well as images containing indicators of celiac-like disease, such as pathologies and/or morphological characteristics. FIG. 7A is an exemplary image of scalloping of the mucosa. Scalloping of the mucosa may be a morphology that indicates a celiac-like disease. FIG. 7B is an exemplary image of mosaic patterning of the mucosa. In celiac-like diseases, the surface pattern of the small intestine mucosa develops a mosaic-like pattern. Mosaic patterning of the mucosa may be a morphology that indicates a celiac-like disease. FIG. 7C is an exemplary image of villous atrophy of the SB mucosa. FIGS. 8A and 8B are graphical representations of normal villi 802 and atrophied villi 804. The normal villi 802 contain large numbers of capillaries that, for example, absorb the amino acids and glucose produced by digestion. Villous atrophy occurs when the villi erode away and significantly reduce the amount of surface area for absorption of nutrients, as shown in FIG. 8B. Villous atrophy of the mucosa may be a pathology which indicates a celiac-like disease. Images such as the exemplary ones shown in FIGS. 7A-7C may be labeled and used for training machine learning systems, such as classical machine learning systems, convolutional neural networks, and/or deep learning neural networks, so that images like these can be classified as containing the pathologies and/or the mucosa morphological characteristics shown in FIGS. 7A-7C.

Figure 9:
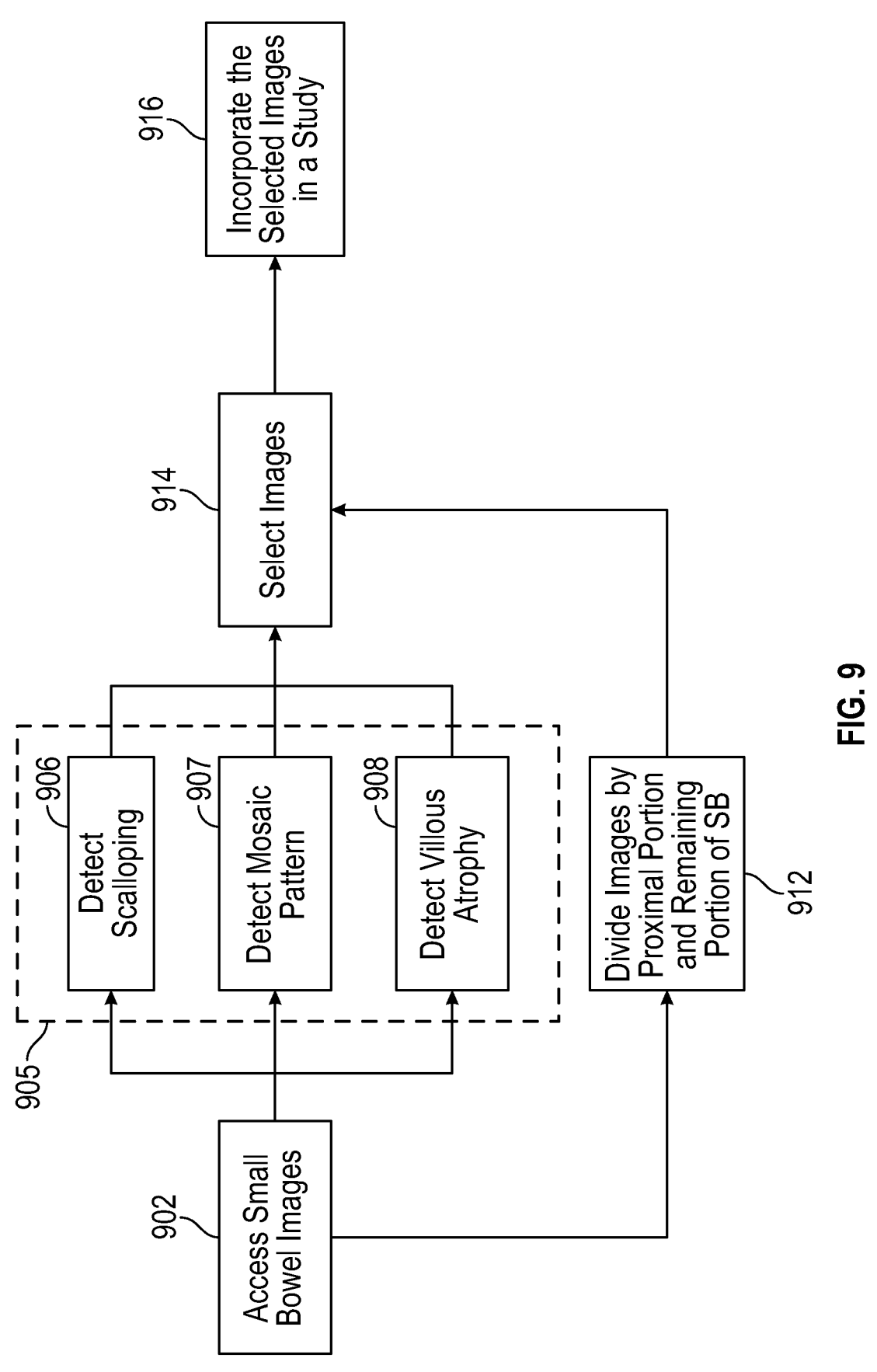
FIG. 9 is a flow diagram of an exemplary operation for identifying images containing indicators of a celiac-like disease, in accordance with aspects of the disclosure.

The flow diagram of FIG. 9 shows a computer implemented method for identifying images containing indicators of a celiac-like disease, such as images containing pathologies and/or morphological characteristics of a celiac-like disease. The identified images can be included in a study to be presented to a physician for evaluating and diagnosing whether a patient has a celiac-like disease. Persons skilled in the art will appreciate that one or more operations of the method may be performed in a different order, repeated, and/or omitted without departing from the scope of the disclosure. Other variations are contemplated to be within the scope of the disclosure. The operations of FIG. 9 can be implemented by a computing system, e.g., computing system 300 (FIGS. 2 and 3), that analyzes medical images captured in vivo via a CE procedure. It will be understood that the illustrated operations can be implemented by other systems and components thereof as well.

Initially, at step 902, the operation includes accessing a consecutive set of images (e.g., a time series of images) of a small bowel captured by a CE device. Techniques for identifying images of a small bowel from a stream of images of a GIT are described in co-pending U.S. Patent Application No. 63/018,890, filed May 1, 2020, which is hereby incorporated by reference in its entirety. Such techniques, and other technique which persons skilled in the art will recognize, can be used to provide the small bowel images accessed at step 902.

Next, at step 905, the operation includes, for each image of the consecutive set of small bowel images 902, detecting indicators of a celiac-like disease by providing one or more classification scores/probabilities which indicate the extent/probability that the image includes various celiac indicators, including scalloping of mucosa 906, mosaic pattern of mucosa 907, and/or villous atrophy 908. The detection of indicators may be performed based on classification scores/probabilities output by one or more convolutional neural networks (e.g., FIG. 5), deep learning neural network(s) (e.g., FIG. 6), or any suitable machine learning system or algorithm (e.g., classical machine learning) configured to detect one or more indicators of a celiac-like disease. For example, as described above, a CNN may be trained using villous atrophy images and images which do not include villous atrophy, a separate CNN may be trained using scalloping images and images which do not include scalloping, and/or a separate CNN may be trained using mosaic patterning images and images which do not include mosaic patterning. In various methods, a CNN may be trained using, for example, villous atrophy images, scalloping images, and/or mosaic patterning images, and such a CNN may provide classification scores/probabilities indicating probabilities that an image includes two or more classification categories among: scalloping, mosaic patterning, villous atrophy, and/or negative for all (i.e., negative for scalloping, mosaic patterning, and villous atrophy). Other variations are contemplated to be within the scope of the present disclosure. The detection of step 905 is exemplary and other pathologies and/or morphological characteristics of the mucosa may be detected. In various embodiments, not all of the indicators 906-908 may be detected, such that only one or two of the indicators 906-908 may be detected.

In various aspects, rather than detecting indicators in step 905, step 905 may, instead, access classification scores/probabilities for the images 902. For example, the images may be pre-processed before the operations of FIG. 9. The pre-processing may output classification scores/probabilities, as described above, and may associate the one or more classification scores/probabilities with the images. Such classification scores/probabilities can be accessed by the operation of FIG. 9.

The classification scores/probabilities are utilized in step 914, which will be described in more detail later herein.

As explained above, the proximal portion of the SB refers to and includes a portion of the small bowel from the beginning of the small bowel to a point before the halfway point of the small bowel, such that the length of the proximal portion of the small bowel is less than half of the physical length of the small bowel. As used herein, the "remaining portion" of the small bowel refers to the portions of the small bowel other than the proximal portion of the small bowel. Accordingly, the physical length of the remaining portion of the SB would be longer than the length of the proximal portion of the SB.

Referring to step 912, the operation includes dividing the accessed small bowel images into two groups: images of the proximal portion of the SB, and images of the remaining portion of the SB. For example, the proximal portion of the SB can be a predetermined percentage of the length of the SB, such as twenty percent (20%) or another percentage. In the case where the proximal portion of the SB is 20% of the length of the SB, the remaining portion of the SB would be 80% of the length of the SB. In aspects, the proximal portion of the SB may be an anatomical portion of the SB, such as the duodenum, which is generally about five percent (5%) of the SB. In aspects, the proximal portion of the SB may include the duodenum and a portion of the jejunum and/or the entire jejunum. Persons skilled in the art will recognize various techniques for identifying images of a proximal portion of the small bowel from a stream of images of the small bowel. For example, motion analysis can be performed on the images of the small bowel to determine or estimate amount of movement of the capsule endoscopy device between images. The motion analysis can map the stream of small bowel images to the physical length of the small bowel, thereby enabling the selection of images of a particular portion of the small bowel. Other techniques are contemplated to be within the scope of the present disclosure for dividing images of the small bowel into two or more groups representing different portions of the small bowel. For example, other techniques may include identifying an anatomically distinct transition between the portions or estimating the relative small bowel length traversed by the capsule based on knowledge of relative length of each portion, among others.

At step 914, the operation includes selecting certain of the accessed images based on the results of steps 905 and 912. The operations of step 912 may be performed before, in parallel with, or after the operations of step 905 described above. Step 914 can be implemented by various embodiments and some embodiments are described below. Depending on the particular embodiment or combination of embodiments, portions of step 914 may be performed in parallel with portions of step 905 or portions of step 912.

In accordance with aspects of the present disclosure, in various embodiments of the operation of step 914, the operation can select small bowel images based on thresholds of image scores and/or quotas. For example, an image can be selected if it has a scalloping score/probability, a mosaic patterning score/probability, and/or a villous atrophy score/probability that is over one or more thresholds. In various embodiments, an image can be selected if at least one of these scores/probabilities satisfies a threshold to select that image. As an example of multiple thresholds, an image can be selected if the scalloping score/probability is greater than a first threshold value and, at the same time, the mosaic patterning score/probability is greater than a second threshold value. In various embodiments, each of a scalloping score/probability, a mosaic patterning score/probability, and a villous atrophy score/probability can have a separate threshold value that must be satisfied for an image to be selected.

In various embodiments, images may be selected in accordance with a separation threshold. For example, a separation threshold may prevent an image from being selected if it is separated from an already-selected image by less than a separation threshold value. A separation threshold operates to diversify the selected images for a reader's consideration and to reduce occurrences of selected images or multiple selected images showing the same instances of a disease indicator.

In various embodiments, images may be selected in accordance with a quota. As mentioned above, the selected images are included in a study that is reviewed by a reader. Presenting too many images to a reader may cause a reader to lose focus and miss information in the images. In accordance with aspect of the present disclosure, the operation of step 914 may select images until a quota is filled.

In various embodiments, the operation of step 914 can select images from among images that are identified as being in the proximal portion of the small bowel in step 912. Diseases of the small bowel, such as celiac-like diseases, usually begin in a proximal portion of the small bowel. Accordingly, if a small bowel has a celiac-like disease, images that are in a proximal portion of the small bowel have a greater likelihood of showing indicators of the celiac-like disease. In various embodiments, images of the proximal portion of the small bowel can be selected based on various criteria, such as one or more of the criteria described above herein.

In accordance with aspects of the present disclosure, the operation of step 914 can select images which represent the proximal portion of the SB, such as images spaced across the proximal portion of the small bowel. In various embodiments, the selected images may be evenly spaced across the proximal portion of the SB or may be unevenly spaced across the proximal portion of the SB. For example, as mentioned above, motional analysis can map the stream of small bowel images to the physical length of the small bowel. Such a mapping can be used to select the images representing the proximal portion of the small bowel. Such a selection of images will provide the reader with a sampling of images across the proximal portion of the small bowel and assist the physician in diagnosing the patient and in identifying or spotting indicators of a celiac-like disease, even at the initial stages of the disease.

In various embodiments, the operation of step 914 can select images for a proximal portion of a small bowel and can select images for a remaining portion of the small bowel. For example, a first set of rules can be used to select images of the proximal portion of the SB, and a second set of rules can be used to select images of at least the remaining portion of the SB, where the first set or rules and the second set of rules are different from each other. More generally, a first set of rules can be used to select images of a first portion of the SB, and a second set of rules can be used to select images of a second portion of the SB, where the first set or rules and the second set of rules are different from each other. The first set of rules and the second set of rules can utilize the various embodiments and aspects disclosed in connection with block 914 of FIG. 9. Other variations are contemplated to be within the scope of the present disclosure.

An example of an operation for selecting images representing a proximal portion of the small bowel is shown in FIG. 10. The operation of FIG. 10 is exemplary and may be optional. Each of steps 1020-1050 of FIG. 10 may be optional. Referring to FIG. 10, at block 1010, the operation involves selecting images spaced across a proximal portion of small bowel. In various embodiments, the spaced images can be evenly spaced or approximately evenly spaced. At block 1020, the operation may involve, for each spaced image, selecting a grouping of images surrounding the image, such as a grouping of a predefined number of images, e.g., ten images or another number of images. At block 1030, the operation may optionally involve, for each grouping of images, deselecting images in the grouping with obscured small bowel tissue. In various embodiments, machine learning algorithms, such as a deep learning neural network (e.g., FIG. 6) can be used to identify images containing bubbles or other content. Persons skilled in the art will understand how to train and implement such neural networks. Such machine learning techniques can be used to identify images with obscured small bowel tissue. Such images may be then deselected. At block 1040, the operation may involve, for each grouping of images, selecting at least one of the remaining images based on classification scores/probabilities, such as scores/probabilities of the image containing scalloping of mucosa, scores/probabilities of the image containing mosaic patterning of mucosa, and/or scores/probabilities of the image containing villous atrophy, as described above herein. At block 1050, the operation can optionally include the selected image(s) from each group in a study. The operation of FIG. 10 is exemplary, and variations are contemplated to be within the scope of the present disclosure.

Referring again to FIG. 9, the aspects and embodiments described above in connection with step 914 can be combined in various ways. For example, certain embodiments can apply one or more of score/probability thresholds, separation threshold, quota, quota for a proximal portion of the SB, quota for a remaining portion of the SB, spaced selection (e.g., FIG. for a proximal portion of the SB, spaced selection for a remaining portion of the SB, and/or spaced selection for an entirety of the SB. Two particular embodiments of the operation of step 914 are described below in connection with FIG. 11 and FIG. 12. Whichever embodiment or combination of embodiments is implemented for step 914, the images selected by step 914 may be included in a study to be presented to a reader, as shown in step 916 of FIG. 9.

FIG. 11 shows an exemplary operation for the image selection process of FIG. 9. Aspects of the image selection process (e.g., block 914) of FIG. 9, described above, are applicable to the operation of FIG. 11. At block 1110, the operation involves accessing images of a proximal portion of a small bowel. At block 1120, the operation involves selecting images representing the proximal portion of the small bowel. Such images may provide coverage of the proximal portion of the small bowel. For example, the images may be evenly spaced across the proximal portion of the small bowel or may be unevenly spaced across the proximal portion of the small bowel. At block 1130, the operation involves accessing images of at least a remaining portion of the small bowel, which may be images spanning an entire length of the small bowel. At block 1140, the operation involves selecting from among images of at least the remaining portion of the SB based on classification scores/probabilities. In various embodiments, selection of block 1140 can apply other criteria, such as one or more criteria described in connection with block 914 of FIG. 9. At block 1150, the operation involves including the images selected at block 1120 and the images selected at block 1140 in a study to be presented to a reader. The operation of FIG. 11 can be implemented by a computing system, such as the computing system of FIG. 3.

FIG. 12 shows another exemplary operation for the image selection process of FIG. 9. Aspects of the image selection process (e.g., block 914) of FIG. 9, described above, are applicable to the operation of FIG. 12. At block 1210, the operation involves accessing images of a proximal portion of a small bowel. At block 1220, the operation involves selecting images from among the images of the proximal portion of the SB based on a less restrictive/less selective set of rules. At block 1230, the operation involves accessing images of a remaining portion of the small bowel. At block 1240, the operation involves selecting images from among the images of the remaining portion of the small bowel based on a more restrictive/more selective set of rules. In various embodiments, the selection processes of blocks 1220 and 1240 can be based on various criteria, such as one or more of the criteria described above in connection with block 914 of FIG. 9. In various embodiments, the selection process of block 1220 may be less restrictive in the sense that more information about the small bowel may be conveyed by the images selected by block 1220, than by the images selected by block 1240. In various embodiments, the selection process of block 1220 may be less restrictive in the sense that a more comprehensive representation of the proximal portion of the small bowel may be selected by block 1220, and a less comprehensive representation of the remaining portion of the small bowel may be selected by block 1240. In various embodiments, the selection process of block 1220 may be less restrictive in the sense that fewer criteria are used to select images in block 1220, and more criteria are used to select images in block 1240. For example, the selection process of block 1220 may include only a classification score threshold, whereas the selection process of block 1240 may include a classification score threshold as well as at least one other criterion such as a separation threshold or a quota. In various embodiments, the selection process of block 1220 may be less restrictive in the sense that a less restrictive level of a criteria is used to select images in block 1220, and a more restrictive level of the same criteria is used to select images in block 1240. Such criteria may be, for example, scores threshold or image quota. Accordingly, a threshold score value may be determined to select images in block 1220 while a threshold score value y>x may be determined to select images in block 1240; a quota x may be determined for the number of images to be selected in block 1120 and a quota y may be determined in block 1240, while the ratio between x and the relative length of the proximal portion (with respect to SB) is higher than the ratio between y and the relative length of the remaining portion of the SB (with respect to SB).

Other variations of blocks 1220 and 1240 are contemplated to be within the scope of the present disclosure. At block 1250, the operation involves including the images selected at block 1220 and the image selected at block 1240 in a study to be presented to a reader. The operation of FIG. 12 can be implemented by a computing system, such as the computing system of FIG. 3.

The operation of FIG. 12 is exemplary, and variations are contemplated to be within the scope of the present disclosure.

In various aspects, a set of CE images indicating celiac-like diseases (generated according to the disclosure) selected according to the disclosed systems and methods may be used to, for example, assist in, facilitate, or enable diagnosing celiac-like diseases. For example, if images selected and displayed show villous atrophy, scalloping and/or mosaic pattern, a physician may obtain a biopsy or perform any other medical exam or procedure required to diagnose a celiac-like diseases. In aspects, the selected set of CE images indicating celiac-like diseases may be used to monitor and/or to evaluate the progress of mucosal healing after, e.g., the onset of treatment (e.g., medication) or after following a diet. This may be achieved by performing multiple CE procedures on a patient, e.g., prior to and following an onset of treatment or diet. The status of the patient as reflected by the selected set of images presented to a physician (or as reflected in a report generated based on a study including the selected set of images) for each procedure may be compared. In aspects, the selected set of CE images indicating celiac-like diseases may be used to diagnose a refractory celiac, e.g., celiac which may be resistant or unresponsive to a predefined period of treatment including strict gluten-free diet. In aspects, the selected set of CE images indicating celiac-like diseases may be used to evaluate the extent of a celiac-like disease. In aspects, the disclosed systems and methods may include the determination of disease extent based on the number of images identified to indicate celiac-like disease or based on evaluation of the relative capsule progress from one image to the other. In aspects, the selected set of CE images indicating celiac-like diseases may be used to identify areas where a pathology and/or morphology occurs that can be biopsied or flagged for closer inspection. Accordingly, the disclosed systems and methods may include the determination of a location for biopsy or a biopsy site. In aspects, the selected set of CE images indicating a celiac-like diseases, which may be inherited (like celiac), may be used as a screening tool for relatives of patients.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for detecting indicators of a disease characterized by a presence of villous atrophy in images of a gastrointestinal tract (GIT), the method comprising:

accessing a consecutive set of images of at least a portion of the GIT comprising a small bowel comprising a proximal portion and a remaining portion, wherein each image of the consecutive set of images is associated with one or more classification scores and each classification score of the one or more classification scores is indicative of the respective associated image including a respective indicator of a disease characterized by the presence of villous atrophy;

selecting a subset of images, from the consecutive set of images, based on the one or more classification scores of each image of the consecutive set of images;

identifying, from the consecutive set of images, a segment of images which includes all of the images that show the proximal portion of the small bowel;

selecting a plurality of images, from the identified segment of images, that represent the proximal portion of the small bowel, wherein the selecting the plurality of images from the segment of images that represents the proximal portion of the small bowel includes selecting images spaced across the proximal portion of the small bowel;

selecting a second plurality of images, from the consecutive set of images, that represent the remaining portion of the small bowel;

displaying the plurality of images selected from the identified segment of images, the second plurality of images, and the subset of images on a display;

selecting a first subset of images from the images that show the proximal portion of the small bowel based on application of a first set of rules, at least one rule of the first set of rules based on the one or more classification scores associated with each image; and selecting a second subset of images from the images that represent the remaining portion of the small bowel based on application of a second set of rules different from the first set of rules, at least one rule of the second set of rules based on the one or more classification scores associated with each image, wherein the second set of rules is more selective than the first set of rules.

2. The method of claim 1, wherein the proximal portion of the small bowel includes a duodenum.

3. The method of claim 1, wherein the disease characterized by the presence of villous atrophy includes at least one of human immunodeficiency virus, common variable immune deficiency, Chron's disease, or celiac disease.

4. The method of claim 1, wherein selecting the plurality of images from the identified segment of images is based on the one or more classification scores.

5. The method of claim 1, wherein selecting images spaced across the proximal portion of the small bowel includes selecting images of the proximal portion of the small bowel which are not obscured.

6. The method of claim 1, further comprising detecting one or more indicators of a disease associated with the presence of villous atrophy in the consecutive set of images based on at least one of a deep learning classifier or a classical machine learning classifier.

7. The method of claim 1, wherein selecting the plurality of images from the identified segment of images includes uniformly sampling the proximal portion of the small bowel based on time or length of the small bowel, where length is based on at least one of a number of images in the consecutive set of images or an estimated advance of a capsule endoscopy device along the small bowel.

8. The method of claim 1, wherein selecting the plurality of images from the identified segment of images includes:

dividing the plurality of images from the identified segment of images into a predetermined number of sampling points; and for each sampling point, selecting one or more images from a predetermined range of images surrounding the sampling point.

9. The method of claim 1, wherein the indicator includes at least one of scalloping of the mucosa of the small bowel, mosaic patterning of the mucosa of the small bowel, or atrophy of villi of the small bowel.

10. A system for detecting indicators of a disease characterized by a presence of villous atrophy in images of a gastrointestinal tract (GIT), the system comprising:

one or more processors; and at least one memory storing instructions which, when executed by the one or more processors, cause the system at least to:

access a consecutive set of images of at least a portion of the GIT comprising a small bowel comprising a proximal portion and a remaining portion, wherein each image of the consecutive set of images is associated with one or more classification scores and each classification score of the one or more classification scores is indicative of the respective associated image including a respective indicator of a disease characterized by the presence of villous atrophy;

select a subset of images, from the consecutive set of images, based on the one or more classification scores of each image of the consecutive set of images;

identify, from the consecutive set of images, a segment of images which includes all of the images that show the proximal portion of the small bowel;

select a plurality of images, from the identified segment of images, that represent the proximal portion of the small bowel, wherein the selecting the plurality of images from the segment of images that represents the proximal portion of the small bowel includes selecting images spaced across the proximal portion of the small bowel;

select a second plurality of images, from the consecutive set of images, that represent the remaining portion of the small bowel;

display the plurality of images selected from the identified segment of images, the second plurality of images, and the subset of images on a display;

select a first subset of images from the images that show the proximal portion of the small bowel based on application of a first set of rules, at least one rule of the first set of rules based on the one or more classification scores associated with each image; and selecting a second subset of images from the images that represent the remaining portion of the small bowel based on application of a second set of rules different from the first set of rules, at least one rule of the second set of rules based on the one or more classification scores associated with each image, wherein the second set of rules is more selective than the first set of rules.

11. The system of claim 10, wherein the proximal portion of the small bowel includes a duodenum.

12. The system of claim 10, wherein the disease characterized by the presence of villous atrophy includes at least one of human immunodeficiency virus, common variable immune deficiency, Chron's disease, or celiac disease.

13. The system of claim 10, wherein selecting the plurality of images from the identified segment of images is based on the one or more classification scores.

14. The system of claim 10, wherein selecting images spaced across the proximal portion of the small bowel includes selecting images of the proximal portion of the small bowel which are not obscured.

15. The system of claim 10, wherein the instructions, when executed by the one or more processors, further cause the system at least to:

detect one or more indicators of a disease associated with the presence of villous atrophy in the consecutive set of images based on at least one of a deep learning classifier or a classical machine learning classifier.

16. The system of claim 10, wherein selecting the plurality of images from the identified segment of images includes uniformly sampling the proximal portion of the small bowel based on time or length of the small bowel, where length is based on at least one of a number of images in the consecutive set of images or an estimated advance of a capsule endoscopy device along the small bowel.

17. The system of claim 10, wherein selecting the plurality of images from the identified segment of images includes:

dividing the plurality of images from the identified segment of images into a predetermined number of sampling points; and for each sampling point, selecting one or more images from a predetermined range of images surrounding the sampling point.

18. The system of claim 10, wherein the indicator includes at least one of scalloping of the mucosa of the small bowel, mosaic patterning of the mucosa of the small bowel, or atrophy of villi of the small bowel.

\* \* \* \* \*